(12) United States Patent
Akimoto et al.

(10) Patent No.: US 11,879,753 B2
(45) Date of Patent: Jan. 23, 2024

(54) SENSOR AND SENSOR MODULE

(71) Applicant: KABUSHIKI KAISHA TOSHIBA, Tokyo (JP)

(72) Inventors: Yosuke Akimoto, Yokohama Kanagawa (JP); Hiroki Kudo, Kawasaki Kanagawa (JP); Hiroaki Yamazaki, Yokohama Kanagawa (JP); Kentaro Nakajima, Ashiya Hyogo (JP); Kohei Suzuki, Daito Osaka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 377 days.

(21) Appl. No.: 17/176,878

(22) Filed: Feb. 16, 2021

(65) Prior Publication Data
US 2021/0318279 A1 Oct. 14, 2021

(30) Foreign Application Priority Data

Apr. 10, 2020 (JP) .................. 2020-071084

(51) Int. Cl.
*G01D 11/30* (2006.01)
*G01N 33/00* (2006.01)
*G01D 11/24* (2006.01)
*G01N 35/00* (2006.01)

(52) U.S. Cl.
CPC ............ *G01D 11/30* (2013.01); *G01D 11/245* (2013.01); *G01N 33/005* (2013.01); *G01N 33/0009* (2013.01); *G01N 33/0027* (2013.01); *G01N 2035/00306* (2013.01)

(58) Field of Classification Search
CPC ...... G01D 11/30; G01D 11/245; G01D 11/24; G01N 33/0009; G01N 33/005; G01N 33/0027; G01N 2035/00306
See application file for complete search history.

(56) References Cited

U.S. PATENT DOCUMENTS

2020/0083549 A1 3/2020 Kawai et al.
2020/0116685 A1* 4/2020 Wei ..................... G01M 3/2892
2021/0318282 A1* 10/2021 Akimoto ............ G01N 33/0045

FOREIGN PATENT DOCUMENTS

JP        2015-12504 A    1/2015
WO   WO 2018-110441 A1   6/2018

* cited by examiner

*Primary Examiner* — Benjamin R Schmitt
(74) *Attorney, Agent, or Firm* — Finnegan, Henderson, Farabow, Garrett & Dunner, LLP

(57) ABSTRACT

A sensor includes a handhole part and a sensor module. The handhole part includes an inner wall and a holder. The holder is located at the inner wall. The sensor module is provided in the handhole part. The sensor module includes a held part held by the holder, a housing connected with the held part, a sensor circuit provided in the housing and including a gas sensor element, and a battery configured to supply electrical power to the sensor circuit. A gap is between the inner wall and the housing and between the housing and a first member under the housing.

18 Claims, 3 Drawing Sheets

SENSOR AND SENSOR MODULE

CROSS-REFERENCE TO RELATED APPLICATIONS

This application is based upon and claims the benefit of priority from Japanese Patent Application No. 2020-071084, filed on Apr. 10, 2020; the entire contents of which are incorporated herein by reference.

FIELD

Embodiments described herein relate generally to a sensor and a sensor module.

BACKGROUND

For example, there is a sensor that detects a gas such as hydrogen, etc. More stable operation of the sensor is desirable.

DETAILED DESCRIPTION

Figure 1:
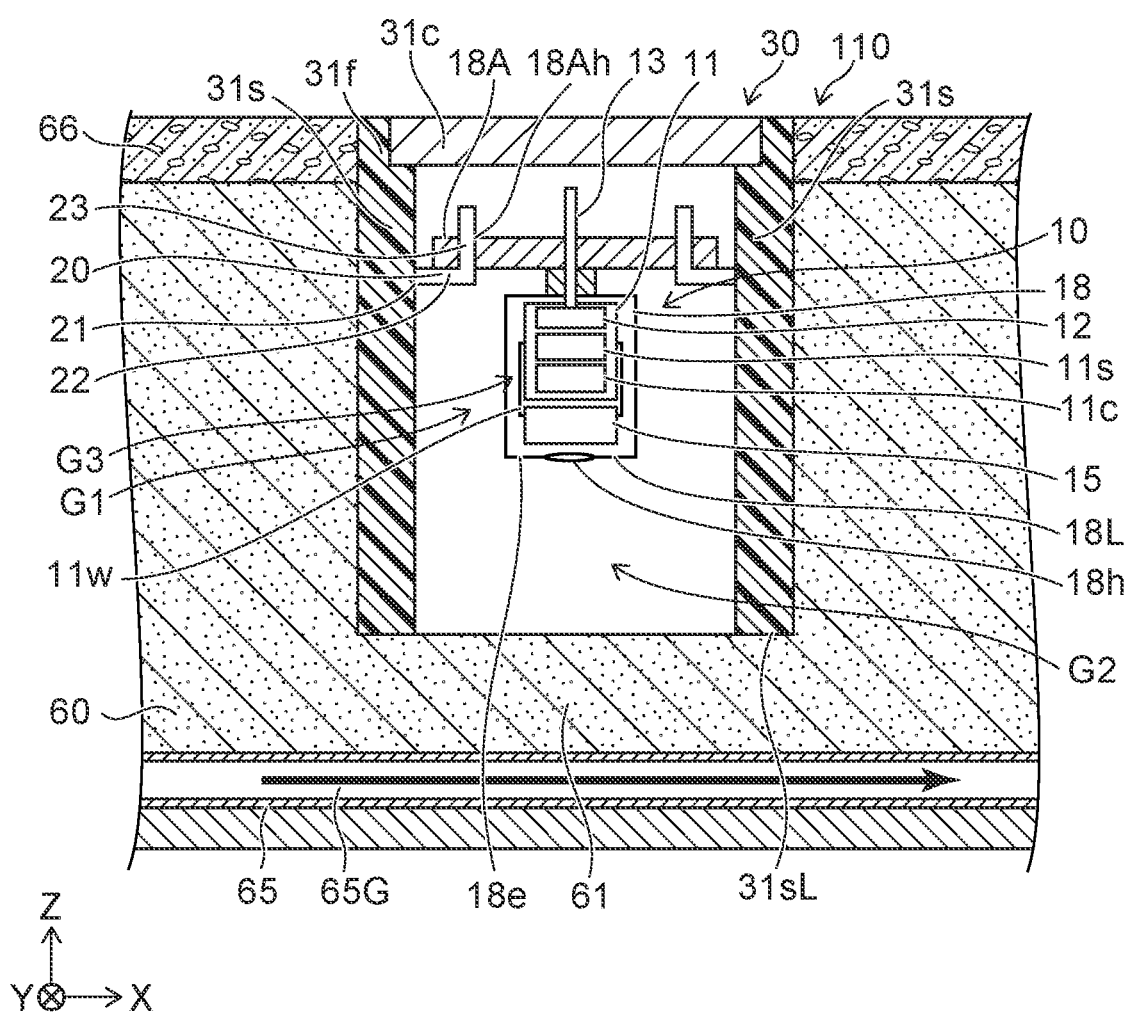
FIG. 1 is a schematic cross-sectional view illustrating a sensor according to a first embodiment.

According to one embodiment, a sensor includes a handhole part, and a sensor module. The handhole part includes an inner wall and a holder. The holder is located at the inner wall. The sensor module is provided in the handhole part. The sensor module includes a held part held by the holder, a housing connected with the held part, a sensor circuit provided in the housing, the sensor circuit including a gas sensor element, and a battery configured to supply electrical power to the sensor circuit. A gap is between the inner wall and the housing and between the housing and a first member under the housing.

According to one embodiment, a sensor module includes a held part, a housing connected with the held part, a sensor circuit provided in the housing and including a gas sensor element, and a battery configured to supply electrical power to the sensor circuit. The sensor module is capable of being located in the handhole part by the held part being held so that a gap is formed between the housing and an inner wall of a handhole part and between the housing and a first member under the housing.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic cross-sectional view illustrating a sensor according to a first embodiment.

Figure 2:
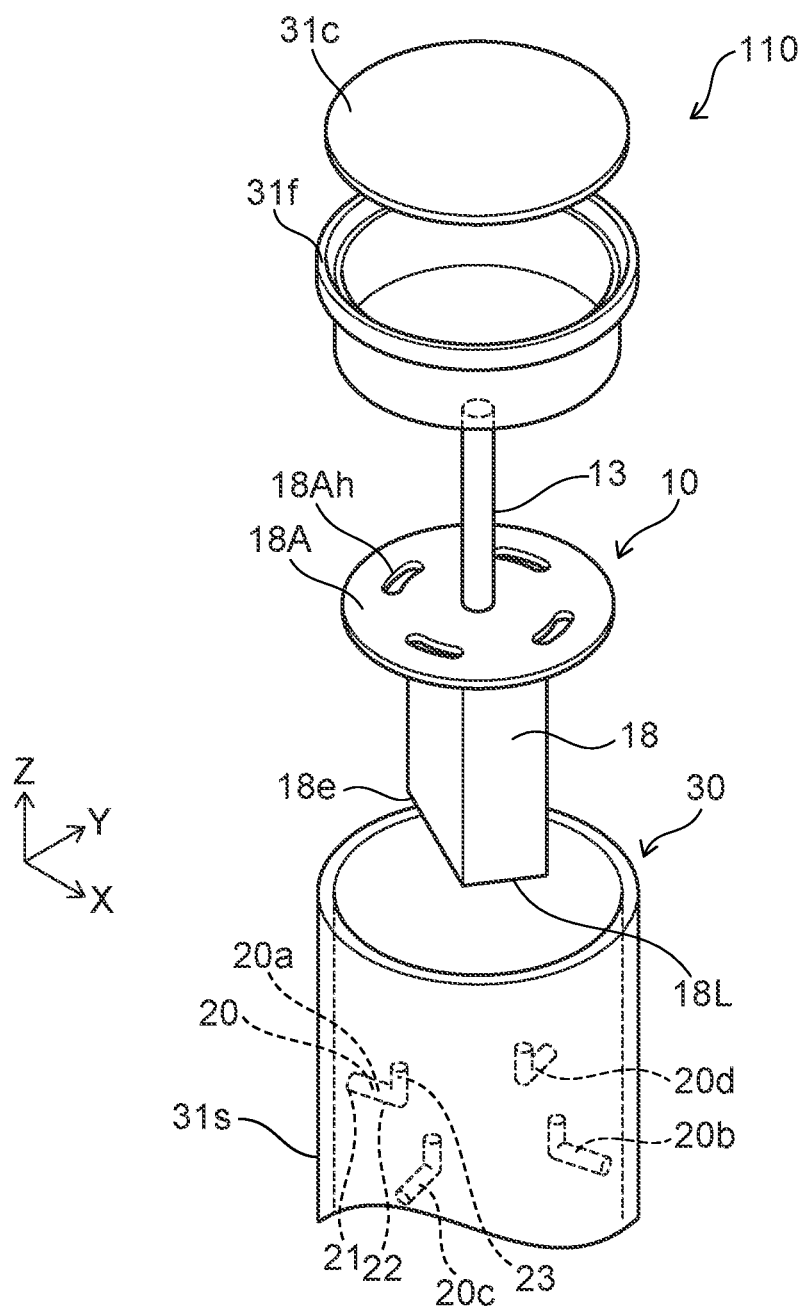
FIG. 2 is a schematic perspective view illustrating the sensor according to the first embodiment.

FIG. 2 is a schematic perspective view illustrating the sensor according to the first embodiment.

Figure 3:
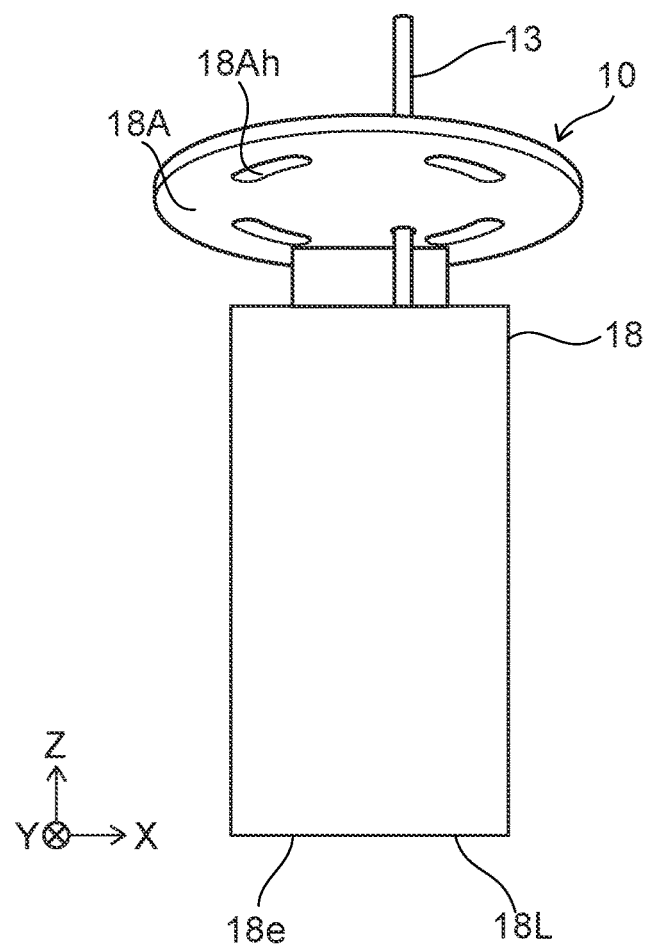
FIG. 3 is a schematic perspective view illustrating a portion of the sensor according to the first embodiment.

FIG. 3 is a schematic perspective view illustrating a portion of the sensor according to the first embodiment.

As shown in FIG. 1, the sensor 110 according to the embodiment includes a handhole part 30 and a sensor module 10.

For example, the handhole part 30 is buried in an installation object 60. The installation object 60 is a ground surface, a floor, a wall, etc. The handhole part 30 includes, for example, an inner wall 31s and a lid part 31c. The inner wall 31s is, for example, tubular. For example, the lid part 31c is in the same layer as a surface layer 66 (which may be, for example, paving, etc.) of the installation object 60.

The direction in which the inner wall 31s extends is taken as a Z-axis direction. One direction perpendicular to the Z-axis direction is taken as an X-axis direction. A direction perpendicular to the Z-axis direction and the X-axis direction is taken as a Y-axis direction.

According to the embodiment, the handhole part 30 further includes a holder 20. The holder 20 is located at the inner wall 31s. For example, the holder 20 is fixed to the inner wall 31s.

The handhole part 30 is, for example, circular (including flattened-circular) in the X-Y plane. According to the embodiment, the planar shape of the handhole part 30 is arbitrary.

The sensor module 10 is located in the handhole part 30. The sensor module 10 includes a held part 18A, a housing 18, a sensor circuit 11, and a battery 15. The housing 18 is connected with the held part 18A. In the example, the housing 18 is under the held part 18A.

The sensor circuit 11 is located in the housing 18. The sensor circuit 11 includes a gas sensor element 11s. For example, the gas sensor element 11s is configured to detect hydrogen. Thus, in one example, the sensor module 10 is configured to detect hydrogen. According to the embodiment, the sensor module 10 may be configured to detect another gas.

In the example, the sensor circuit 11 includes a control circuit 11c. The control circuit 11c controls the gas sensor element 11s. The control circuit 11c is, for example, a microcomputer.

The battery 15 is configured to supply electrical power to the sensor circuit 11. For example, the battery 15 and the sensor circuit 11 are electrically connected by wiring 11w.

The holder 20 holds the sensor module 10. For example, the holder 20 holds the held part 18A and the housing 18 above a first member 61 that is under the housing 18. The first member 61 is under the housing 18. The first member 61 is, for example, a ground surface. The first member 61 is, for example, at least one of a ground surface, a floor, or a wall.

According to the embodiment, a gap is between the inner wall 31s and the housing 18 and between the housing 18 and the first member 61 under the housing 18. For example, a gap G1 is between the inner wall 31s and the housing 18. A gap G2 is between the housing 18 and the first member 61 under the housing 18. Air is in the gaps G1 and G2. The housing 18 is separated from the inner wall 31s via the gap G1. The housing 18 is separated from the first member 61 via the gap G2.

For example, it was found that condensation easily occurs at the sensor module 10 located in the handhole part 30, etc. It is considered that this is caused by the reduction of the temperature of the sensor module 10 and around the sensor module 10. For example, the heat capacity of the first member 61 is large. For example, the temperature of the first member 61 becomes low at night, etc. The temperature of the inner wall 31s that contacts the first member 61 (the ground surface, etc.) also becomes low. For example, it is considered that condensation occurs at the sensor module 10 when the temperature of the sensor module 10 decreases as the temperature around the sensor module 10 decreases. In particular, it is considered that misoperations of the sensor circuit 11 easily occur when condensation occurs at the sensor circuit 11. For example, it is considered that the value that is detected by the sensor circuit 11 easily becomes inaccurate.

According to the embodiment, the housing 18 of the sensor module 10 is separated from the inner wall 31s via the gap G1 and separated from the first member 61 via the gap G2. Therefore, the sensor module 10 is not thermally continuous with the surroundings. Even when the temperature of the surroundings decreases, the temperature of the sensor module 10 is not easily linked to the temperature of the surroundings. According to the embodiment, the electrical power from the battery 15 is supplied to the sensor circuit 11. The temperature of the sensor circuit 11 easily increases due to the supplied electrical power. Therefore, the condensation can be suppressed particularly around the sensor circuit 11. Because the condensation is suppressed, abnormal operations of the sensor circuit 11 can be suppressed. The values that are detected by the sensor circuit 11 are accurate. According to the embodiment, a sensor can be provided in which stable operations are possible.

For example, the temperature of the control circuit 11c increases particularly easily due to the electrical power supplied from the battery 15. Due to the heat of the control circuit 11c, the temperature of the gas sensor element 11s is prevented from becoming excessively low; and the condensation can be effectively suppressed.

As shown in FIG. 1, a gap G3 is provided between the housing 18 and the sensor circuit 11. Thereby, the sensor circuit 11 is thermally isolated from the housing 18. The temperature of the sensor circuit 11 is prevented from becoming low.

In the example as shown in FIG. 1, at least a portion of the held part 18A is on the holder 20. For example, the holder 20 includes a first portion 21 and a second portion 22. The first portion 21 is fixed to the inner wall 31s. At least a portion of the held part 18A is on the second portion 22.

For easier viewing in FIG. 2, the handhole part 30 and the sensor module 10 are drawn as being separated from each other. The holder 20 includes a third portion 23. The second portion 22 is between the first portion 21 and the third portion. For example, the third portion 23 extends upward from the second portion 22. As shown in FIG. 1, at least a portion of the third portion 23 passes through a held part hole 18Ah of the held part 18A. Due to such a structure, the held part 18A is more stably held by the holder 20.

Multiple holders 20 are provided in the example as shown in FIG. 2. The multiple holders 20 include, for example, a first holder 20a and a second holder 20b. The direction from the first holder 20a toward the second holder 20b crosses the upward direction (the Z-axis direction) from the first member 61 toward the housing 18. In the example, the held part 18A includes multiple held part holes 18Ah. For example, at least a portion of one of the multiple holders 20 passes through one of the multiple held part holes 18Ah.

As shown in FIG. 2, the multiple holders 20 may include a third holder 20c. The direction from the first holder 20a toward the second holder 20b crosses the direction from the first holder 20a toward the third holder 20c. The multiple holders 20 may include a fourth holder 20d. The direction from the first holder 20a toward the second holder 20b crosses the direction from the third holder 20c toward the fourth holder 20d.

As shown in FIG. 1, a lower end 18e of the housing 18 is higher than a lower end 31sL of the inner wall 31s. A stable gap G2 is obtained thereby.

It is favorable for the thermal conductivity of the holder 20 holding the sensor module 10 to be low. For example, at least a portion of the holder 20 includes a resin. The thermal conduction between the sensor module 10 and the surroundings can be suppressed thereby.

It is favorable for at least a portion of the held part 18A to include a resin. The thermal conduction between the sensor module 10 and the surroundings can be suppressed thereby.

As shown in FIG. 1, the housing 18 includes a lower portion 18L. For example, the lower portion 18L faces the first member 61. At least a portion of the bottom part of the handhole part 30 may be between the lower portion 18L and the first member 61. The lower portion 18L includes a hole 18h. A gas can pass through the hole 18h.

For example, a gas pipe 65 is provided in the installation object 60. The sensor 110 is located on the gas pipe 65. A gas 65G passes through the gas pipe 65. When the gas 65G leaks from the gas pipe 65, the gas 65G reaches the sensor module 10 via the first member 61 of the installation object 60. The gas 65G can reach the sensor circuit 11 by passing through the hole 18h. The gas 65G is detected by the sensor circuit 11. The sensor 110 is configured to detect a gas leak.

As shown in FIG. 1, the sensor module 10 may include a wireless communication circuit 12 and an antenna 13. In the example, the wireless communication circuit 12 is in the housing 18. The wireless communication circuit 12 is configured to transmit a signal corresponding to a value detected by the sensor circuit 11. The antenna 13 is connected with the wireless communication circuit 12. Transmission is performed via the antenna 13. In the example as shown in FIGS. 1 and 3, at least a portion of the antenna 13 is above the held part 18A. More stable communication can be performed thereby.

As shown in FIGS. 1 and 2, a flange 31f is provided on the inner wall 31s. The lid part 31c is mounted to the flange 31f. As shown in FIG. 1, for example, the flange 31f is buried in the surface layer 66 of the installation object 60.

Figure 4:
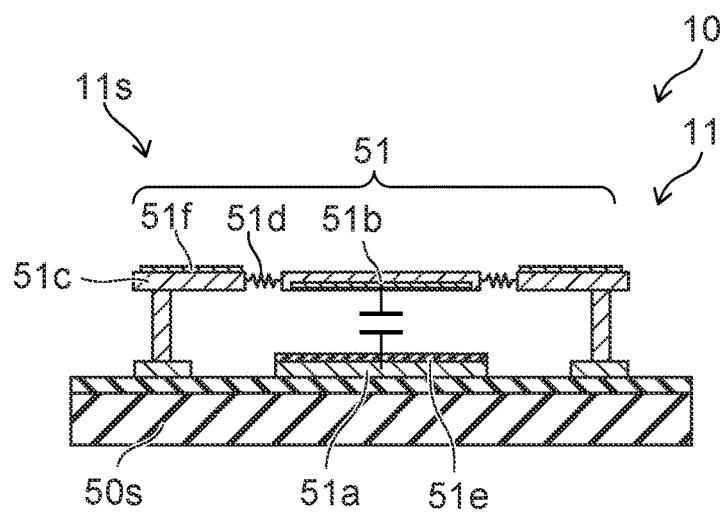
FIG. 4 is a schematic cross-sectional view illustrating a portion of the sensor according to the first embodiment.

FIG. 4 is a schematic cross-sectional view illustrating a portion of the sensor according to the first embodiment.

FIG. 4 illustrates a portion of the sensor module 10. In the sensor circuit 11 of the sensor module 10 as shown in FIG. 4, the gas sensor element 11s includes a first element 51.

The first element 51 includes a fixed electrode 51a, a movable electrode 51b, a holding member 51c, and a connection part 51d. The fixed electrode 51a and the holding member 51c are fixed to a base body 50s. One end of the connection part 51d is fixed to the holding member 51c. Another end of the connection part 51d is connected to the movable electrode 51b. The connection part 51d is, for example, a spring. The movable electrode 51b is held by the holding member 51c and the connection part 51d to be separated from the fixed electrode 51a. In the example, a film 51f is provided at the holding member 51c. The gas 65G to be detected can adsorb to the film 51*f*. For example, when the gas 65G adsorbs to the film 51*f*, physical characteristics of the film 51*f* change, and the distance between the movable electrode 51*b* and the fixed electrode 51*a* changes. The gas 65G to be detected can be detected by detecting the electrical capacitance between the movable electrode 51*b* and the fixed electrode 51*a*. The first element 51 is, for example, a capacitance change-type MEMS (Micro Electro Mechanical Systems) hydrogen sensor element.

The film 51*f* includes, for example, Pd, Cu, and Si. According to the embodiment, the material of the film 51*f* may be determined according to the type of the gas 65G to be detected.

In the example, an insulating film 51*e* is provided at the surface of the fixed electrode 51*a*. Contact of the movable electrode 51*b* with the fixed electrode 51*a* can be suppressed. More stable detection is possible.

As described above, the gas sensor element 11*s* may have a MEMS structure. A small sensor circuit 11 is obtained. For example, the space (e.g., the gap G3) around the sensor circuit 11 can be increased thereby, and the condensation, etc., can be further suppressed.

Second Embodiment

A second embodiment relates to the sensor module 10.

As shown in FIG. 1, the sensor module 10 includes the held part 18A, the housing 18, the sensor circuit 11, and the battery 15. The housing 18 is connected with the held part 18A. The held part 18A is a portion that is held by the holder 20. The sensor circuit 11 is located in the housing 18. The sensor circuit 11 includes the gas sensor element 11*s*. The battery 15 is configured to supply electrical power to the sensor circuit 11. The sensor module 10 can be located in the handhole part 30 by the held part 18A being held so that a gap (the gap G1 and the gap G2) is formed between the housing 18 and the inner wall 31*s* of the handhole part 30 and between the housing 18 and the first member 61 under the housing 18. According to the embodiment, for example, condensation at the sensor circuit 11, etc., can be suppressed. A sensor module is provided in which stable operations are possible.

As shown in FIGS. 1 to 3, for example, the held part 18A includes the held part hole 18Ah. As shown in FIG. 1, at least a portion of the holder 20 can pass through the held part hole 18Ah. Stable holding is obtained.

According to the embodiment, the sensor module 10 that is located inside the handhole part 30 is fixed to be surrounded with an air layer. The sensor module 10 is thermally isolated from the handhole part 30 and the installation object 60 (e.g., soil). For example, the condensation at the sensor module 10 can be suppressed. For example, misdetection is suppressed.

Embodiments may include the following configurations (e.g., technological proposals).

Configuration 1
  A sensor, comprising:
  a handhole part including an inner wall and a holder, the holder being located at the inner wall; and
  a sensor module provided in the handhole part, the sensor module including
    a held part held by the holder,
    a housing connected with the held part,
    a sensor circuit provided in the housing, the sensor circuit including a gas sensor element, and
    a battery configured to supply electrical power to the sensor circuit,
  a gap being between the inner wall and the housing and between the housing and a first member under the housing.

Configuration 2
  The sensor according to Configuration 1, wherein
  at least a portion of the held part is on the holder.

Configuration 3
  The sensor according to Configuration 1, wherein
  the holder includes a first portion and a second portion,
  the first portion is fixed to the inner wall, and
  at least a portion of the held part is on the second portion.

Configuration 4
  The sensor according to Configuration 3, wherein
  the held part includes a held part hole,
  the holder further includes a third portion,
  the second portion is between the first portion and the third portion, and
  at least a portion of the third portion passes through the held part hole.

Configuration 5
  The sensor according to Configuration 4, wherein
  the third portion extends upward from the second portion.

Configuration 6
  The sensor according to Configuration 1 or 2, wherein
  a plurality of the holders is provided,
  the plurality of holders includes a first holder and a second holder, and
  a direction from the first holder toward the second holder crosses an upward direction from the first member toward the housing.

Configuration 7
  The sensor according to Configuration 6, wherein
  the plurality of holders includes a third holder, and
  the direction from the first holder toward the second holder crosses a direction from the first holder toward the third holder.

Configuration 8
  The sensor according to Configuration 6, wherein
  the plurality of holders includes a fourth holder, and
  the direction from the first holder toward the second holder crosses a direction from the third holder toward the fourth holder.

Configuration 9
  The sensor according to any one of Configurations 6 to 8, wherein
  the held part includes a plurality of held part holes, and
  at least a portion of one of the plurality of holders passes through one of the plurality of held part holes.

Configuration 10
  The sensor according to any one of Configurations 1 to 9, wherein
  a lower end of the housing is higher than a lower end of the inner wall.

Configuration 11
  The sensor according to any one of Configurations 1 to 10, wherein
  at least a portion of the holder includes a resin.

Configuration 12
  The sensor according to any one of Configurations 1 to 11, wherein
  at least a portion of the held part includes a resin.

Configuration 13
  The sensor according to any one of Configurations 1 to 12, wherein
  the first member is at least one of a ground surface, a floor, or a wall.

Configuration 14
　The sensor according to any one of Configurations 1 to 13, wherein
　　the housing includes a lower portion facing the first member, and
　　the lower portion includes a hole through which a gas can pass.
Configuration 15
　The sensor according to any one of Configurations 1 to 14, wherein
　　the sensor circuit includes a control circuit controlling the gas sensor element.
Configuration 16
　The sensor according to any one of Configurations 1 to 15, wherein
　　the sensor module includes:
　　　a wireless communication circuit; and
　　　an antenna connected with the wireless communication circuit, and
　　at least a portion of the antenna is above the held part.
Configuration 17
　The sensor according to Configuration 16, wherein
　　the wireless communication circuit is in the housing.
Configuration 18
　The sensor according to any one of Configurations 1 to 16, wherein
　　the gas sensor element has a MEMS structure.
Configuration 19
　The sensor according to any one of Configurations 1 to 17, wherein
　　the sensor module is configured to detect hydrogen.
Configuration 20
　A sensor module, comprising:
　　a held part;
　　a housing connected with the held part;
　　a sensor circuit provided in the housing, the sensor circuit including a gas sensor element; and
　　a battery configured to supply electrical power to the sensor circuit,
　　the sensor module being capable of being located in the handhole part by the held part being held so that a gap is formed between the housing and an inner wall of a handhole part and between the housing and a first member under the housing.
Configuration 21
　The sensor module according to Configuration 19, wherein
　　the held part includes a held part hole, and
　　at least a portion of the holder can pass through the held part hole.

According to embodiments, a sensor and a sensor module can be provided in which stable operations are possible.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as handhole parts, sensor modules, housings, sensor circuits, batteries, holders, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and sensor modules practicable by an appropriate design modification by one skilled in the art based on the sensors, and the sensor modules described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:
1. A sensor, comprising:
　a handhole part including an inner wall and a holder, the holder being located at the inner wall; and
　a sensor module provided in the handhole part,
　the sensor module including
　　a held part held by the holder,
　　a housing connected with the held part,
　　a sensor circuit provided in the housing, the sensor circuit including a gas sensor element, and
　　a battery configured to supply electrical power to the sensor circuit,
　a gap being between the inner wall and the housing and between the housing and a first member under the housing,
　wherein
　　the holder includes a first portion and a second portion,
　　the first portion is fixed to the inner wall,
　　at least a portion of the held part is on the second portion,
　　the held part includes a held part hole,
　　the holder further includes a third portion,
　　the second portion is between the first portion and the third portion, and
　　at least a portion of the third portion passes through the held part hole.
2. The sensor according to claim 1, wherein
at least a portion of the held part is on the holder.
3. The sensor according to claim 1, wherein
the third portion extends upward from the second portion.
4. The sensor according to claim 1, wherein
a plurality of the holders is provided,
the plurality of holders includes a first holder and a second holder, and
a direction from the first holder toward the second holder crosses an upward direction from the first member toward the housing.
5. The sensor according to claim 4, wherein
the plurality of holders includes a third holder, and
the direction from the first holder toward the second holder crosses a direction from the first holder toward the third holder.
6. The sensor according to claim 4, wherein
the plurality of holders includes a fourth holder, and
the direction from the first holder toward the second holder crosses a direction from the third holder toward the fourth holder.

7. The sensor according to claim 4, wherein
the held part includes a plurality of held part holes, and
at least a portion of one of the plurality of holders passes through one of the plurality of held part holes.
8. The sensor according to claim 1, wherein
a lower end of the housing is higher than a lower end of the inner wall.
9. The sensor according to claim 1, wherein
at least a portion of the holder includes a resin.
10. The sensor according to claim 1, wherein
at least a portion of the held part includes a resin.
11. The sensor according to claim 1, wherein
the first member is at least one of a ground surface, a floor, or a wall.
12. The sensor according to claim 1, wherein
the housing includes a lower portion facing the first member, and
the lower portion includes a hole through which a gas can pass.
13. The sensor according to claim 1, wherein
the sensor circuit includes a control circuit controlling the gas sensor element.
14. The sensor according to claim 1, wherein
the sensor module includes:
 a wireless communication circuit; and
 an antenna connected with the wireless communication circuit, and
at least a portion of the antenna is above the held part.
15. The sensor according to claim 14, wherein
the wireless communication circuit is in the housing.
16. The sensor according to claim 1, wherein
the gas sensor element has a MEMS structure.
17. The sensor according to claim 1, wherein
the sensor module is configured to detect hydrogen.
18. A sensor, comprising:
a handhole part including an inner wall and a holder, the holder being located at the inner wall; and
a sensor module provided in the handhole part,
the sensor module including
 a held part held by the holder,
 a housing connected with the held part,
 a sensor circuit provided in the housing, the sensor circuit including a gas sensor element, and
 a battery configured to supply electrical power to the sensor circuit,
a gap being between the inner wall and the housing and between the housing and a first member under the housing,
wherein
 a plurality of the holders is provided,
 the plurality of holders includes a first holder and a second holder,
 a direction from the first holder toward the second holder crosses an upward direction from the first member toward the housing,
 the plurality of holders includes a third holder, and
 the direction from the first holder toward the second holder crosses a direction from the first holder toward the third holder.

\* \* \* \* \*